(12) United States Patent
Remaut et al.

(10) Patent No.: US 9,790,510 B2
(45) Date of Patent: *Oct. 17, 2017

(54) **METHOD TO IMPROVE *LACTOCOCCUS* PRESERVATION**

(71) Applicant: INTREXON ACTOBIOTICS NV, Zwijnaarde (BE)

(72) Inventors: Erik Remaut, Vinderhoute (BE); Dirk Iserentant, Wijgmaal (BE)

(73) Assignee: INTREXON ACTOBIOTICS NV, Zwijnaarde (BE)

( * ) Notice: Subject to any disclaimer, the term of this patent is extended or adjusted under 35 U.S.C. 154(b) by 0 days.

This patent is subject to a terminal disclaimer.

(21) Appl. No.: 14/934,572

(22) Filed: Nov. 6, 2015

(65) Prior Publication Data

US 2016/0076044 A1 Mar. 17, 2016

Related U.S. Application Data

(63) Continuation of application No. 11/660,584, filed as application No. PCT/EP2005/054088 on Aug. 18, 2005, now Pat. No. 9,200,249.

(30) Foreign Application Priority Data

Aug. 20, 2004 (EP) .................................... 04104001
Apr. 12, 2005 (EP) .................................... 05102856

(51) Int. Cl.
C12N 1/04 (2006.01)
C12N 15/74 (2006.01)

(52) U.S. Cl.
CPC ............. *C12N 15/746* (2013.01); *C12N 1/04* (2013.01)

(58) Field of Classification Search
None
See application file for complete search history.

(56) References Cited

U.S. PATENT DOCUMENTS

| 6,133,034 A | 10/2000 | Strom et al. |
| 6,323,001 B1 | 11/2001 | Londesborough et al. |
| 6,605,286 B2 | 8/2003 | Steidler et al. |
| 7,592,013 B2 | 9/2009 | Hans et al. |

FOREIGN PATENT DOCUMENTS

| EP | 1 441 027 | 7/2004 |
| WO | WO 00/60094 | 10/2000 |
| WO | WO 01/02570 | 1/2001 |
| WO | WO 01/65923 | 9/2001 |
| WO | WO 02/090551 | 11/2002 |

OTHER PUBLICATIONS

Andersson et al., The Journal of Biological Chemistry vol. 276, No. 46, Issue of Nov. 16, pp. 42707-42713.
Bermudez-Humaran et al., Infection and Immunity, Apr. 2003, p. 1887-1896 vol. 71, No. 4.
Carcoba et al., Eur. Food Res. Technol. (2000) 211 :433-437.
Chatel, et al. Induction of Mucosal Immune Response after Intranasal or Oral Inoculation of Mice with *Lactococcus lactis* Producing Bovine Beta-Lactoglobulin, Clinical and Diagnostic Laboratory Immunology, vol. 8, No. 3, pp. 545-551, May 2001.
Cibik, et al. "Identification of Mur, an Atypical Peptidoglycan Hydrolase Derived from Leuconostoc citreum," Applied and Environmental Microbiology, vol. 67, No. 2, pp. 858-864, Feb. 2001.
Geoffroy, et al. "Use of Green Fluorescent Protein to Tag Lactic Acid Bacterium Strains under Development as Live Vaccine Vectors," Applied and Environmental Microbiology, vol. 66, No. 1, pp. 383-391, Jan. 2000.
Hugenholtz, et al. "Nutraceutical Production with Food-grade Microorganisms," Current Opinion in Biotechnology, vol. 13, pp. 497-507, 2002.
Kandror et al., PNAS, Jul. 23, 2002, vol. 99 (No. 15), pp. 9727-9732.
Klerebezem et al., Applied and Environmental Microbiology, Nov. 1997, p. 4581-4584 vol. 63, No. 1.
Kuipers, et al. "Quorum Sensing-controlled Gene Expression in Lactic Acid Bacteria," Journal of Biotechnology, vol. 64, pp. 15-21, 1998.
Le Loir, et al. "Protein Secretion in *Lactococcus lactis*: an efficient way to increase the overall heterologous protein production," Microbial Cell Factories, vol. 4, No. 2, on line publication Jan. 4, 2005, 13 pages.
Martin et al., International Journal of Food Microbiology 112 (2006) 35-43.
Mierau, et al. "10 Years of the Nisin-controlled Gene Expression System (NICE) in *Lactococcus lactis*," Appl Microbiol Biotechnol, vol. 68, pp. 705-717, 2005.
Padilla et al., Applied and Environmental Microbiology, Jan. 2004, p. 370-376 vol. 70, No. 1.
Steidler, et al., Science 289, 1352 (2000)), Fig 2, p. 1353.
Waterfield et al., Gene, 165 (1995) 9-15.
Garcia-Quintans, et al. "The Citrate Transport System of *Lactococcus lactis* subsp. *lactis* Biovar Diacetylactis is Induced by Acid Stress," Applied and Environmental Microbiology, vol. 64, No. 3, pp. 850-857, Mar. 1998.
Li, et al. "Glutathione Protects *Lactococcus lactis* Against Oxidative Stress," Applied and Environmental Microbiology, vol. 69, No. 10, pp. 5739-5745, Oct. 2003.

(Continued)

*Primary Examiner* — Irene Marx
(74) *Attorney, Agent, or Firm* — Drinker Biddle & Reath LLP

(57) ABSTRACT

*Lactococcus lactis* strains with improved preservation characteristics, and improved acid and bile salt tolerance are disclosed. More specifically, a *L. lactis* strain having a heterologous trehalose-6-phosphate synthase gene and/or a trehalose-6-phosphate phosphatase gene, results in an accumulation of trehalose in the cytoplasm and/or in the cytoplasmic membrane. A *L. lactis* strain, having an internal trehalose concentration of at least 10 mg per gram cells (w/w) is disclosed.

18 Claims, 5 Drawing Sheets

(56) References Cited

OTHER PUBLICATIONS

Miyoshi, et al., "Controlled Production of Stable Heterologous Proteins in *Lactococcus lactis*," Applied and Environmental Microbiology, vol. 68, No. 6, pp. 3141-3146, Jun. 2002.
Rallu et al. "Acid- and Multistress-Resistant Mutants of *Lactococcus lactis*: Identification of Intracellular Stress Signals," Molecular Microbiology, vol. 35, No. 3, pp. 517-528, 2000.
International Search Report issued Feb. 1, 2006 in International Application No. PCT/EP2005/054088.

METHOD TO IMPROVE *LACTOCOCCUS* PRESERVATION

RELATED APPLICATIONS

This application is a divisional of U.S. application Ser. No. 11/660,584, filed Mar. 12, 2007 which is the U.S. National Phase under 35 U.S.C. §371 of International Application PCT/EP2005/054088, filed Aug. 18, 2005, which claims priority of EP 04104001.5, filed Aug. 20, 2004 and EP 05102856.1, filed Apr. 12, 2005.

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND OF THE INVENTION

Reference to Sequence Listing

This application incorporates by reference the sequence listing submitted as ASCII text filed via EFS-Web on Nov. 6, 2015. The Sequence Listing is provided as a file entitled "nlo00100d1.txt," created on Nov. 6, 2015, and which is approximately 4 kilobytes in size.

Field of the Invention

The present invention relates to *Lactococcus lactis* strains with improved preservation characteristics, and improved acid and bile salt tolerance. More specifically, the invention relates to a *L. lactis* strain comprising a heterologous trehalose-6-phosphate synthase gene and/or a trehalose-6-phosphate phosphatase gene, resulting in an accumulation of trehalose in the cytoplasm and/or in the cytoplasmic membrane. It further relates to a *L. lactis* strain, whereby said trehalose accumulation results in an internal trehalose concentration of at least 10 mg per gram cells (ww).

Description of the Related Art

*Lactococcus lactis* is a mesophilic and microaerophilic fermenting lactic acid bacterium. It is commonly occurring in nature, especially on plant material. The bacterium is extensively used in food fermentations, especially in the dairy industry. Moreover, there is an increasing interest for its use in nutraceuticals, as medication to treat vaginal infections or as carrier for the delivery of biological active molecules. In all those cases, there is a need for highly viable starter cultures, or pharmaceutical formulations comprising a high proportion of viable bacteria. One of the major drawbacks of *L. lactis* however is a rapid drop in viability during storage, or during processing for tablet formation. The drop in viability is even more dramatic when the bacterium after lyophilisation is submitted to additional stress such as high acidity or the presence of bile salts. Several methods have been proposed to overcome this problem. Attempts to improve the viability are made both at the level of culture conditions of the bacteria as well as at the level of the processing. Gaudu et al. (2002) disclose that Lactococci grown via respiration survive markedly better after long time storage than fermenting cells. This long time survival is probably due to the induction of cytochromes which may protect the cells from oxidative stress. Li et al. (2003) demonstrated that the presence of intracellular glutathion, which is also protecting against oxidative stress, can also result in an improved viability upon storage.

Another approach to improve the viability of Lactococci upon storage lays in the adaptation of the spray-drying process, and in the use of process aids, such as microcristalline cellulose, carboxymethylcellulose, hydroxypropylmethylcellulose acetate succinate, or sodium alginate, which may be used to coat the bacterial particles.

Although these processes certainly lead to an improvement of the storage, none of the solutions is sufficient, and there is a further need of methods that can lead to an improved storage of *Lactococcus*, especially in those cases where the bacterium is used for the delivery of biological active compounds in medical applications.

Trehalose (α-D-glucopyranosyl-1,1-α-D-glucopyranosyde) is a non-reducing disaccharide that occurs in a large variety of organisms, ranging from bacteria to invertebrate animals. Trehalose, sometimes in combination with dextran is often used as and externally added cryopreservant. Externally added trehalose functions as a saccharide matrix (Conrad et al., 2000), and exerts it protective effect especially during freeze drying, where it acts as a glass former. Moreover, trehalose is well recognized as stress metabolite, and it has been extensively studied in fungi, especially in *Saccharomyces cerevisiae*. High concentrations of internal trehalose do improve the storage capacity and result in a higher viability upon cryopreservation. However, it is important to note that externally added trehalose rarely leads to internal trehalose accumulation in micro-organisms, either because it is not taken up, or it is metabolized rapidly after uptake.

Externally added trehalose has been used, amongst others, for preservation of *Lactobacillus* during freeze drying (Conrad et al., 2000) and for the stabilization of *Lactococcus* during freezing (EP 1441027). However, although the role of internal trehalose in eukaryotic cells is well documented, there are no data available about a positive role in preservation in prokaryotes. Padilla et al. (2004) have recently shown that an overproduction of trehalose can be obtained in the trehalose producing and secreting gram-positive bacterium *Corynebacterium glutanicum*, by expressing the otsA and otsB genes of *Escherichia coli* in this species. However, in this case, the expression of the *E. coli* genes leads to an increase of the endogenous synthase and phosphatase activities, and to an increase of the existing endogenous trehalose production. Moreover, the effect of the overproduction of trehalose on the storage of *C. glutanicum* is unknown.

*Lactococcus lactis* is able to utilize trehalose (Andersson et al., 2001), but up to now, no trehalose synthesizing *Lactococcus lactis* strain has been described. Indeed, no trehalose-6-phosphate synthase or trehalose-6-phosphate phosphatase genes has been identified, which are essential steps in the trehalose production starting from glucose-6-phosphate, a metabolite that is present in *L. lactis*. Surprisingly we found that, by transfer of and expression in *L. lactis* of the otsA (trehalose-6-phosphate synthase) and otsB (trehalose-6-phosphate phosphatase) genes of *Escherichia coli* a significant trehalose accumulation can be obtained. Even more surprisingly, this trehalose accumulation leads to an important improvement of the viability under stress conditions and during storage, under several storage conditions. Therefore, internal trehalose accumulation seems an ideal method to improve the storage and stress resistance characteristics of *Lactococcus* sp in general and *L. lactis* in particular.

A first aspect of the invention is an isolated strain of *Lactococcus* sp., preferably *L. lactis*, comprising an internal trehalose concentration of at least 10 mg trehalose, preferably 30 mg trehalose, more preferably 40 mg trehalose, most preferably 50 mg trehalose per gram wet weight of cells (i.e 50 mg trehalose, preferably 150 mg trehalose, more preferably 200 mg trehalose, most preferably 250 mg trehalose per gram dry weight of cells). Internal trehalose concentration as used here means that the trehalose is synthesized or taken up by the bacteria, and present in the cytoplasm and/or in the cytoplasmic membrane of the bacteria. Internal trehalose differs clearly form exogenous trehalose, added to the medium, which may stick to the outside of the bacterial cell wall but is not incorporated in the bacteria. Preferably, said internal trehalose is endogenously synthesized trehalose.

A further aspect of the invention is an isolated strain of *Lactococcus* sp, preferably *L. lactis*, comprising a heterologous trehalose-6-phosphate synthase and/or trehalose-6-phosphate phosphatase gene. A gene as used here is a DNA sequence that comprises at least the coding sequences for a functional protein. Preferably, said genes are operably linked to a promoter that is functional in *L. lactis*. Operably linked refers to a juxtaposition wherein the components so described are in a relationship permitting them to function in their intended manner. A promoter sequence "operably linked" to a coding sequence is ligated in such a way that expression of the coding sequence is achieved under conditions compatible with the promoter sequence. Said promoter may be an inducible promoter or a constitutive promoter. Both genes may be operably linked to one single promoter, as an operon, or they may be placed under the control of two promoters, which may be identical or different. One preferred embodiment is an isolated strain of *Lactococcus* sp, preferably *L. lactis* strain, whereby said genes are placed under the control of the nisin inducible promoter of *L. lactis*. Another preferred embodiment is a *L. lactis* strain, whereby said genes are placed under the control of the constitutive P1 promoter. Preferably, said trehalose-6-phosphate synthase gene is the otsA gene of *E. coli*, and the trehalose-6-phosphate phosphatase gene is the otsB gene of *E. coli*. Method for transformation of *Lactococcus* sp are known to the person skilled in the art, and include, but are not limited to electroporation. The heterologous genes may be situated on a self replicating plasmid, or may be integrated in the bacterial genome.

Another aspect of the invention is the use of internal trehalose accumulation in *Lactococcus* sp to improve the storage characteristics of *Lactococcus*. Preferably, said *Lactococcus* sp. is *L. lactis*. Trehalose accumulation as used here means an internal concentration of trehalose of at least 10 mg trehalose, preferably 30 mg trehalose, more preferably 40 mg trehalose, most preferably 50 mg trehalose per gram wet weight of cells. Preferably, the accumulation of internal trehalose is obtained by expression of a heterologous trehalose-6-phosphate synthase and/or trehalose-6-phosphate phosphatase gene, even more preferably by expression of the otsA and/or the otsB gene of *E. coli*.

Alternatively, it may be obtained by external addition of trehalose to the growth medium, and by replacing the trehalose-6-phosphate phosphorylase by a trehalose-6-phoshpatase phosphatase gene such as OtsB, and by growth of this strain on trehalose and another carbon source, preferably maltose. Indeed, growth on trehalose as such doesn't lead to trehalose accumulation, due to rapid metabolization after uptake. Moreover, in *L. lactis*, trehalose is phosphorylated during uptake to yield trehalose-6-phosphate. However, by allowing the uptake of trehalose with the concomitant phosphorylation to trehalose-6-phosphate, but blocking the further down stream processing by converting the trehalose-6-phosphate to trehalose, while the trehalose-6-phosphate phosphorylase activity is inactivated, an accumulation of internal trehalose will be obtained. Still another possibility for the accumulation of trehalose in *L. lactis* is the transformation of the bacterium with a heterologous non-phosphorylating trehalose transporter, such as the *Sinorhizobium meliloti* trehalose ABC transporter encoded by the thuEFGK operon (Genbank accession number AF175299; Jensen et al., 2002), preferably combined with the inactivation of the trehalose phosphotransferase, and the growth of the transformed strain on trehalose and another carbon source, preferably lactose. Improvement of the storage characteristics as used here can be any storage, such as, but not limited too storage in growth medium, freezing, freeze drying or spray drying. Preferably, said storage is freeze drying. Improvement of storage can be measured by growing the *L. lactis* strain under conditions resulting in internal trehalose accumulation, freeze-drying the strain, and measuring the evolution of the viability of the strain for at least 4 weeks during storage at 4° C., at 10% RH. Still another aspect of the invention is the use of internal trehalose accumulation in *Lactococcus* sp. to improve the stress resistance of *Lactococcus* sp. Preferably, said *Lactococcus* sp is *L. lactis*. Stress resistance as used here can be any kind of stress. As a non limiting example, it can be stress induced by cold, stress by freezing, stress by spray drying, stress by freeze drying, stress by highly acidic pH (below pH 3.5, preferably below pH 3.2, even more preferably below pH 3.0), stress by the presence of bile salts, or a combination of those stresses, either in parallel or successive. Preferably, said stress is stress by highly acidic pH, even more preferably said stress is stress by the presence of bile salts, most preferably said stress is stress by freeze drying. A special embodiment is the use of internal trehalose accumulation in *Lactococcus* sp. to improve the stress resistance of *Lactococcus* sp. to freeze drying, followed by acid stress and/or presence of bile salts. Preferably, said *Lactococcus* sp. is *L. lactis*. Those stress conditions mimic the conditions the bacteria will encounter when used for delivery in the intestine.

Still another aspect of the invention is the use of an isolated strain of *Lactococcus* sp, preferably *L. lactis* strain according to the invention for the delivery of a prophylactic and/or therapeutic molecule. Preferably, said use is the use of an isolated strain of *Lactococcus* sp., preferably *L. lactis*, for the preparation of a medicament for delivery of a prophylactic and/or therapeutic molecule. Delivery of biological active polypeptides has been described in WO97/14806. The use of a strain, according to the invention has the advantage that the production of the prophylactic and/or therapeutic molecule is significantly higher, both when calculated per colony forming unit (cfu) or per ml culture. A preferred embodiment is the use of an isolated strain of *Lactococcus* sp., preferably *L. lactis*, for the preparation of a medicament for delivery of a prophylactic and/or therapeutic molecule, whereby said strain additionally carries a self-containing feature, such as the thyA mutation, disclosed in WO02/090551.

EXAMPLES

Example 1: Cloning of the Trehalose-Biosynthesis Genes from Escherichia coli onto the Lactococcal Expression Plasmid pNZ8048

The DNA sequences encoding the trehalose-biosynthesis genes in Escherichia coli are retrieved from GenBank (Acc. Nr. X69160) (Kaasen et al. 1994).

Escherichia coli strain DH5α (Woodcock et al., 1989) serves as the source of the trehalose biosynthesis genes, otsA and otsB, encoding trehalose-6-phosphate synthase and trehalose-6-phosphate phosphatase, respectively. Genomic DNA is purified from $10^9$ cells with the commercially available Qiagen DNeasy kit (Qiagen, Hilden, Germany) according to the supplier's protocol.

The DNA sequence encompassing otsB-otsA is PCR-amplified with Vent® DNA polymerase (New England Biolabs, Beverly, Mass., USA) and the following primer sequences:
forward primer: 5'-GC CCATGGGTGACAGAACCGTTAACCGAAACC-3', in which GTG is the initiator codon of the otsB cistron and the CCATGG sequence is a NcoI restriction site;
reverse primer: 5'-GC TCTAGACTACGCAAGCTTTGGAAAGGTAGC-3', in which CTA is the complement of the TAG stop codon of the otsA cistron and the TCTAGA sequence is a XbaI restriction site.

Figure 1:
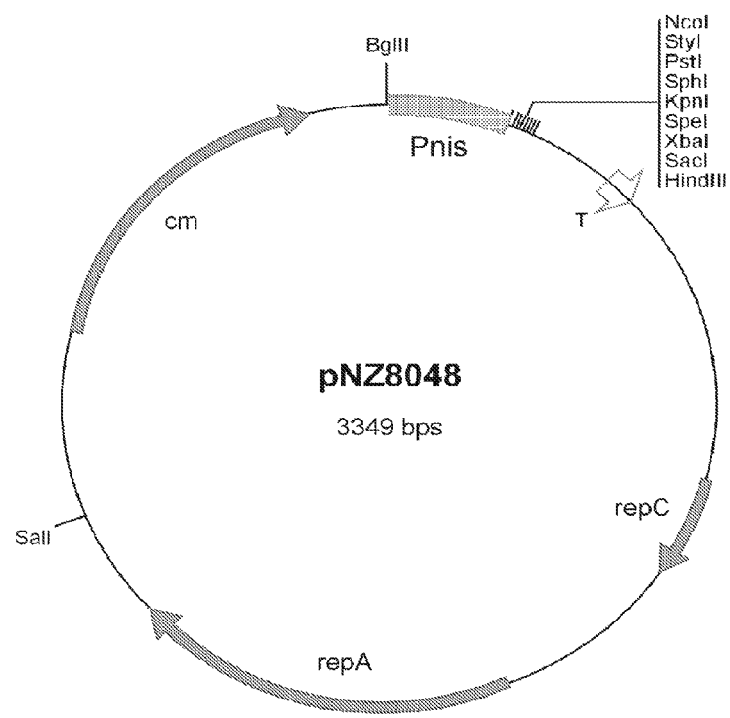
FIG. 1: Plasmid map of pNZ8048

The amplified 2216 bp DNA fragment is digested with NcoI and XbaI, ligated into the NcoI-XbaI opened pNZ8048 vector (Ruyter et al., 1996) (FIG. 1) and transformed by electroporation into L. lactis strain NZ9000 (Wells et al., 1993). Transformants are obtained at 30 C on GM17 (vide infra) plates containing 5 μg chloramphenicol per ml. Plasmid DNA is prepared from the transformants using an SDS-alkaline lysis method adapted for L. lactis; prior to the production of a cleared lysate the cells are pretreated with lysozyme (5 mg/ml) and mutanolysin (100 U/ml). Combined restriction enzyme digest with BglII and XbaI allows identification of the desired recombinant plasmid, designated pNZEcTre0. In this intermediate plasmid construction, the otsB-otsA genes are cloned downstream of the $P_{nis}$ promoter, but the otsB gene is not fused in the correct reading to the ATG initiator codon. The sequence in this region reads: 5'-GGCACTCACCATGGGTGACAGAA-3', in which ACA encodes the $2^{nd}$ amino acid residue of OtsB. Correct fusion of ACA to ATG is obtained following 3 consecutive PCR amplification steps with Vent® DNA polymerase.

Step 1.
Forward primer: 5'-GGCACTCACC ATGACAGAACCGTTAACC-3'
Reverse primer: 5'-GC TCTAGACTACGCAAGCTTTGGAAAGGTAGC-3', in which CTA is the complement of the TAG stop codon of the otsA cistron and the TCTAGA sequence is a XbaI restriction site.

The amplified 2216 bp DNA fragment encompasses the otsB-otsA coding region.

Step 2.
Forward primer: 5'-GC GTCGACGGCAATAGTTACCCTTATTATCAAG-3', in which GTCGAC coincides with the SalI restriction site in pNZEcTre0
Reverse primer: 5'-GGTTAACGGTTCTGT CATGGTGAGTGCC-3', in which CAT is the complement of the initiator codon preceding otsB.

The amplified 1256 bp DNA fragment encompasses the chloramphenicol resistance gene, the $P_{nis}$ promoter and the nisA ribosome-binding site and ATG initiator codon fused to the coding region of otsB.

Step 3.
The 2216 bp DNA fragment from step1 and the 1256 bp DNA fragment from step 2 are mixed in equimolar amounts and subjected to PCR amplification with Vent® DNA polymerase, using 5'-GC GTCGACGGCAATAGTTACCCTTATTATCAAG-3' and 5'-GCTCTAGACTACGCAAGCTTTGGAAAGGTAGC-3' as forward and reverse primers, respectively. The amplified 3444 bp DNA fragment is digested with SalI and XbaI and ligated to a SalI-XbaI fragment, carrying the replicon of pNZ8048. Transformants are obtained in NZ9000 and their plasmids isolated as described above.

Figure 2:
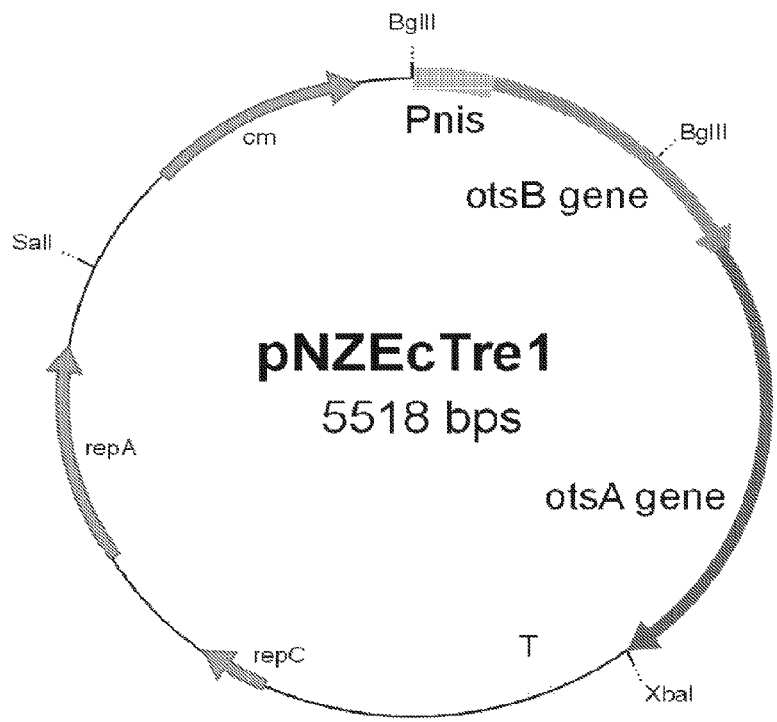
FIG. 2: Plasmid map of pNZEcTre1 whereby the otsB/otsA operon is operably linked to the nisin promoter.

A representative plasmid, whose structure can be identified by restriction enzyme analysis with SalI, XbaI, BglII, NcoI and combinations thereof, is designated pNZEcTre1 (FIG. 2). Finally, the region encompassing the $P_{nis}$ promoter, the nisA ribosome binding site and the junction of the initiator ATG to the otsB cosing region is sequence-verified.

Example 2: Induction of the Cloned Trehalose-Biosynthesis Operon in L. lactis

Figure 3:
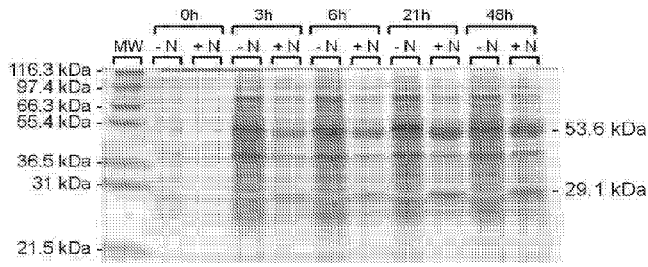
FIG. 3: evaluation of the Trehalose-6-phosphate synthase (marked as 53.6 kDa) and trehalose-6-phosphate phosphatase (marked as 29.1 kDa) protein production, under induced (+N) and non-induced (−N) conditions.
Figure 4:
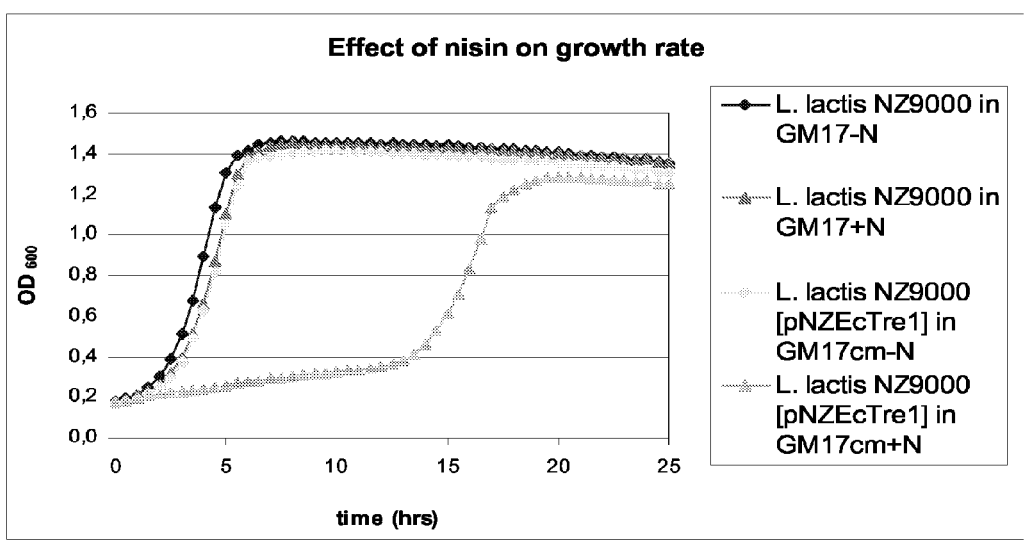
FIG. 4: Effect of nisin, used for promoter induction, on the growth rate of the transformants and the non-transformed control strain (+N: induced, −N: non-induced).

The strains L. lactis NZ9000 [pNZEcTre1] and L. lactis NZ9000 are grown as standing cultures at 30° C. overnight in M17 medium (Difco, Detroit, USA) supplemented with 0.5% glucose (=GM17 medium). The cultures are diluted 100-fold in fresh medium and incubated for another 3 hr at 30° C. The cells are collected by centrifugation and resuspended in the original volume of BM9G medium (M9 medium buffered at pH 8.5 and containing 0.5% glucose; Schotte et al., 2000). Nisin (Aplin&Barrett) is added to a final concentration of 0.4 µg/ml and the cultures are further incubated for up to 48 hr. At several time points samples are taken, the cells collected by centrifugation and lysed by addition of lysozyme (5 mg/ml) and mutanolysin (100 U/ml). SDS-PAGE reveals the nisin-dependent induction (Kuipers et al., 1998) of two additional protein bands in *L. lactis* NZ9000[pNZEcTre1]. Their molecular mass of 53.6 kDa and 29.1 kDa agree with the molecular mass of the *E. coli* trehalose-6-phosphate synthase (OtsA) and trehalose-6-phosphate phosphatase (OtsB), respectively (FIG. 3). They are absent from *L. lactis* NZ9000, irrespective of the addition of nisin. The growth rate of induced NZ9000 [pNZEcTre1] is severely impaired as early as 3 hr after the addition of nisin (FIG. 4). Strain NZ9000 is not affected in its growth rate in the presence of nisin.

Example 3: Optimized Induction Protocol for Trehalose Biosynthesis in *L. lactis*

Strain NZ9000[pNZEcTre1] is grown to saturation as standing culture at 30° C. in GM17Cm (=GM17 containing 5 µg chloramphenicol per ml) and diluted 3-fold into fresh medium containing 0.4 µg nisin/ml. Incubation is continued at 30° C. with shaking at 200 rpm for 8 hr. The growth rate of the culture is unaffected by the addition of nisin. Saturation is reached after 3 hr of incubation. Induction of OtsA and OtsB can be clearly identified by SDS-PAGE.

Concentration of trehalose is determined by converting trehalose to glucose with trehalase (courtesy of J. Thevelein, Dept. of Molecular Microbiology, VIB-K.U.Leuven, Belgium), which is measured by a glucose assay protocol (Trinder, 1969).

The cells are lysed with lysozyme and mutanolysin by incubation in 0.25 M $Na_2CO_3$ for one hr at 37 C and 20 min at 95 C. Cell debris is removed by centrifugation at 13,200 rpm. To one volume of supernatant, 0.5 volume of 1 M HAc and 0.5 volume of a buffer, consisting of 300 mM NaAc and 30 mM $CaCl_2$ pH 5.5, are added. The mixture is incubated for 2 hr at 37 C in the presence of trehalase. Following centrifugation at 13,200 rpm, the supernatant is supplemented with Trinder reagent (glucose oxidase, phenol and 4-aminophenazone; Dialab, Austria) and incubated with shaking for 15 min at 30 C, after which the $OD_{505}$ is automatically recorded in a 96-well VersaMax tunable microplate reader (Molecular Devices, USA)

Figure 5:
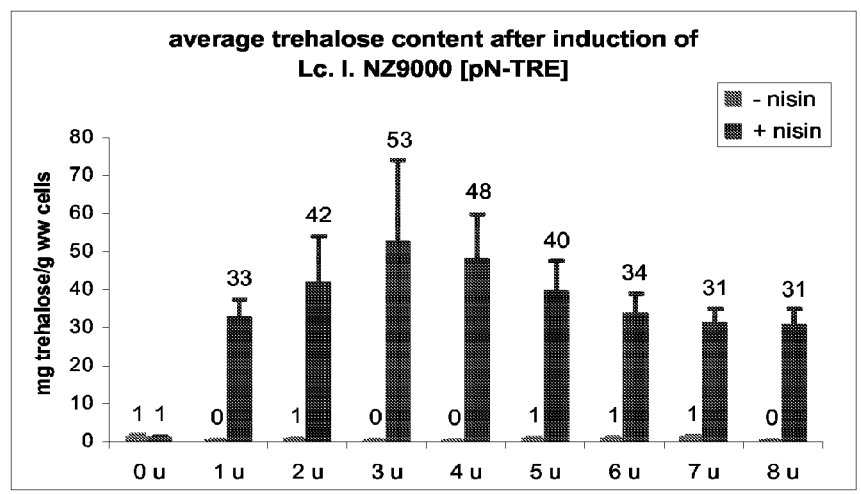
FIG. 5: average trehalose accumulation after induction of L. lactis NZ9000 [pN-TRE]

Experimental trehalose concentrations are read from a calibration curve, obtained with pure trehalose (Sigma-Aldrich Corp. St. Louis, USA), showing a linear correlation between the $OD_{505}$ value and trehalose concentration up to 10 mM trehalose. The accumulation of trehalose in NZ9000 [pNZEcTre1] nisin-induced as described above is shown in FIG. 5. The maximum concentration is reached after 3 hr and coincides with the time point when the culture reaches saturation.

Example 4: Freeze-Drying of *L. lactis* Cultures and Storage Conditions

Strain NZ9000[pNZEcTre1] is grown to saturation as standing culture at 30° C. in GM17Cm and diluted 3-fold into fresh medium with or without nisin (0.4 µg/ml). Incubation is continued at 30° C. with shaking at 200 rpm for 3 hr. The cells are collected by centrifugation at 5000 rpm, resuspended in the original volume 10% (w/v) skim milk (Difco, Becton Dickinson) and kept on ice till ready for freeze-drying.

All freeze-drying runs were performed in triplicate. A sample containing approximately 2 g of cells (wet weight) is filled in sterile vials (glass type 1, Gaash Packaging, Mollem, Belgium). The vials are covered with a lyophilisation stopper (V9032 FM 257/2 SAF1, Bromobutyl with magnesium silicate as filler, Helvoet Pharma, Alken, Belgium). The vials are loaded in the pre-cooled production chamber (−25° C.) of the freeze-dryer (Leybold GT4, Finn-aqua, Santasalo, Sohlberg, Germany) before freezing to −45° C. over a period of 105 min at 1000 mbar. The primary drying (12 hr) is performed at −15° C. and 0.8 to 1 mbar; the secondary drying (9 hr) at 10° C. and 0.1 to 0.2 mbar. After lyophilisation, the vials are closed under vacuum.

The vials are stored at different conditions: (a) 8° C. and 10% relative humidity (RH), (b) 8° C. and 60% RH, (c) 20° C. and 10% RH.

The water content of the freeze-dried culture is determined using a Mettler DL35 Karl Fisher titrator (Mettler-Toledo, Beersel, Belgium). The samples are stirred in the reaction medium for 60 s. Afterwards the water is titrated with Hydranal® Composite 5 (Riedel-de Haën, Seelze, Germany). The analysis is performed in triplicate.

Example 5: Viability of Freeze-Dried Samples of Induced and Non-Induced Cultures, Under Different Storage Conditions To determine the viability in the freeze-dried powder, 0.1 g powder is dissolved in 1 ml sterile water. Viability of the bacteria is determined by following the growth in a Bioscreen (Labsystems). To this end serial dilutions of the cultures are made, inoculated 1/100 in fresh GM17C and loaded in triplicate into the wells of the Bioscreen. $OD_{600}$ values are automatically recorded at given intervals over a 21 hr period. The time necessary to reach an optical density at 600 nm ($OD_{600}$) half way the minimum and maximum $OD_{600}$ (50% time) is calculated based on the exponential growth phase. This 50% time is plotted against the natural logarithm of the viability and the equation of the standard curve is calculated. The viability of a freeze-dried sample is determined based on the standard curve of the starting culture and expressed as % of theoretical. The viability values of the samples as determined by this method corresponds very well with the results obtained by plating and colony counting.

Table 1 summarizes the measured viability of induced (trehalose containing) or non-induced (trehalose free) NZ9000[pNZEcTre1] cultures, freeze-dried and stored under different conditions of temperature and relative humidity. Viability is expressed as percentage of the viability of the respective culture prior to the freeze-drying step.

Figure 6:
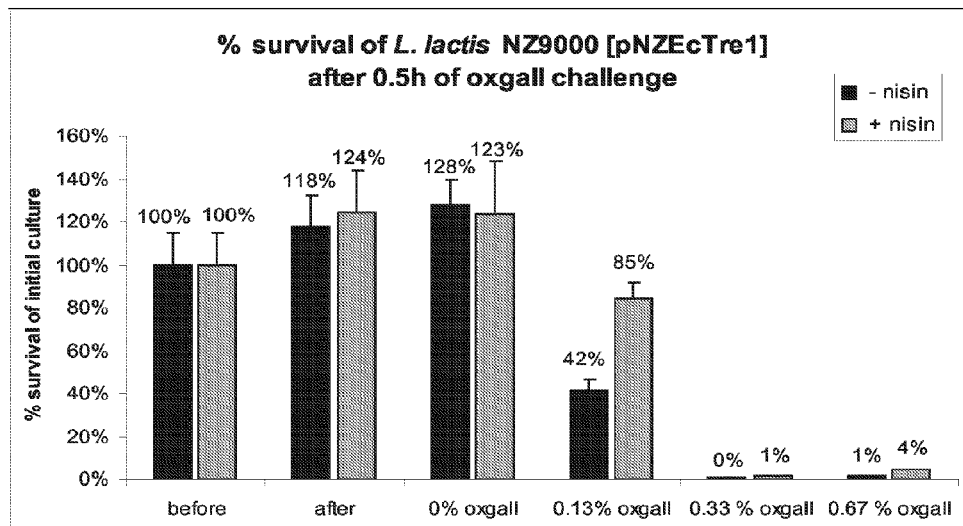
FIG. 6: % survival of L. lactis NZ9000 [pNZEcTre1] after 0.5 h of oxgall challenge. There percentage is calculated as cfu after treatment on initial cfu.

Example 6: Internal Trehalose Accumulation Protects *L. lactis* Against Oxgall Challenge A saturated overnight culture of *L. lactis* NZ9000 [pNZEcTre1] was induced by nisin (0.4 µg/ml) for 3 hrs, at 30° C. and 200 rpm in a shacking water bath. The same culture, without nisin addition, was used as control. The saturated culture was centrifuged and resuspended in sterile double distilled water, with different fysiological concentrations of oxgall. The suspensions were incubated for a total of 4 hours, at 37° C., and samples were taken after 0, 0.5, 2 and 4 hours of incubation. The samples were plated on GM17Cm and the plates were incubated for 24 hours at 30° C. The results were expressed in colony forming units (cfu; table 2) or as percentage viable colonies, relative to the initial amount of cfu's (table 3). A graphical representation of the results after 0.5 hours of oxgall challenge is shown in FIG. 6. Trehalose accumulation in the nisin induced cultures was checked, and reached a concentration of 60 mg/g ww. Although nisin induction on its own results in a reduction of cfu in the initial culture, the survival in the presence of oxgall is clearly better in case of trehalose accumulation.

The results are even more pronounced if the culture is freeze dried before applying the oxgall stress. A saturated overnight culture of *L. lactis* NZ9000 [pNZEcTre1] was induced by nisin for 3 hrs, at 30° C. and 200 rpm in a shacking water bath. The same culture, without nisin addition, was used as control. Both sets of culture was freeze dried, and after freeze drying, the powder was dissolved in sterile double distilled water and different fysiological concentrations of oxgall were added. The suspensions were incubated for a total of 4 hours, at 37° C., and samples were taken after 0, 0.5, 2 and 4 hours of incubation. The samples were plated on GM17Cm and the plates were incubated for 24 hours at 30° C. The results were expressed in colony forming units (cfu; table 4) or as percentage viable colonies, relative to the initial amount of cfu's (table 5).

Figure 7:
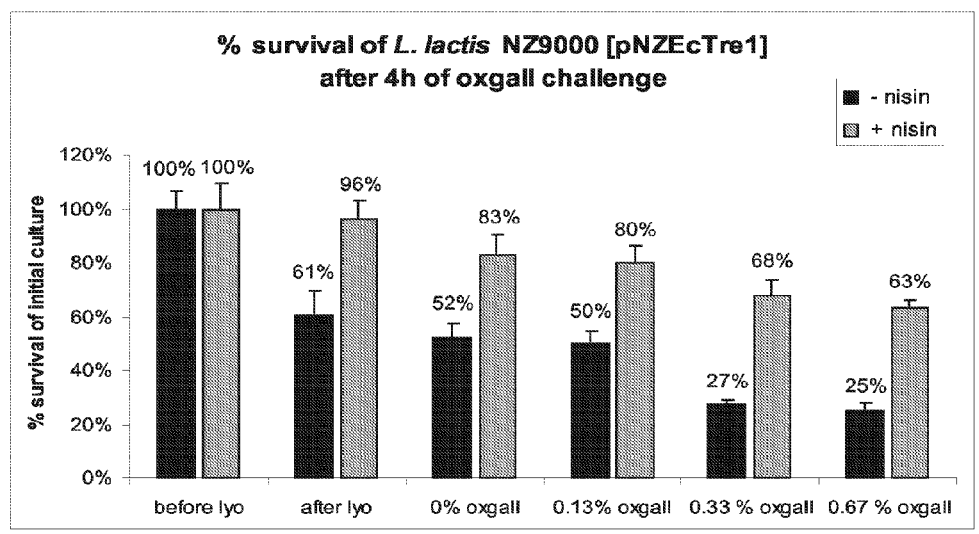
FIG. 7: % survival of L. lactis NZ9000 [pNZEcTre1] after freeze-drying and 4 h of oxgall challenge. There percentage is calculated as cfu after treatment on initial cfu.

The trehalose accumulation in the nisin induced cultures was 58 mg/g ww of cells. Cells with internal trehalose accumulation do maintain their viability better, both after lyophilisation and upon oxgall challenge (Table 4 and 5). FIG. 7 shows the result after 4 hours of oxgall challenge.

Example 7: Internal Trehalose Accumulation Protects *L. lactis* Against High Acidity in the Medium A saturated overnight culture of *L. lactis* NZ9000 [pNZEcTre1] was induced by nisin (0.4 µg/ml) for 3 hrs, at 30° C. and 200 rpm in a shacking water bath. The same culture, without nisin addition, was used as control. Both sets of culture was freeze dried, and after freeze drying, the powder was dissolved in sterile double distilled water and different concentrations of human gastric juice were added (post-operative, pH 2.95)

Figure 8:
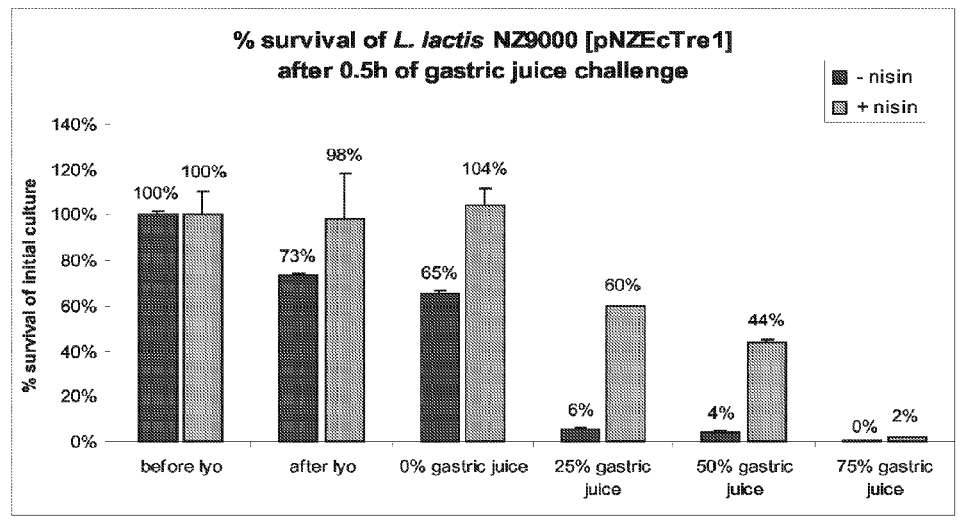
FIG. 8: % survival of L. lactis NZ9000 [pNZEcTre1] after 0.5 h of gastric juice challenge. There percentage is calculated as cfu after treatment on initial cfu.

The suspensions were incubated for a total of 2 hours, at 37° C., and samples were taken after 0, 0.5, 1 and 2 hours of incubation. The samples were plated on GM17Cm and the plates were incubated for 24 hours at 30° C. The results were expressed in colony forming units (cfu; table 6) or as percentage viable colonies, relative to the initial amount of cfu's (table 7). A graphic representation of the relative results (% cfu after the treatment calculated on initial cfu) after 0.5 hour is given in FIG. 8. Internal trehalose accumulation clearly protects *L. lactis* against the high acidity of the gastric juice

Example 8: Internal Trehalose Insures a Higher Productivity of a Prophylactic and/or Therapeutic Molecule after Freeze Drying Construction of pT1hIL10aPxA The build up of plasmid pT1hIL10aPxA is analogous to the plasmid, containing murine IL-10 (Schotte et al., 2000) It contains the hIL-10 gene fused to the usp45 secretion leader, preceded by the coliphage T7 gene 10 ribosome binding site and the P1 promoter. The sequence of the IL-10 gene is a synthetic one in which codon usage was adapted to the preferred codon usage in *L lactis* and in which the proline residue—the first amino acid of the mature protein in native human IL-10—was replaced by an alanine residue. The plasmid was transformed in *L. lactis* strain MG1363, according to Wells et al., 1993.

Construction of pNZEcTre1-hIL10aPxA

Figure 11:
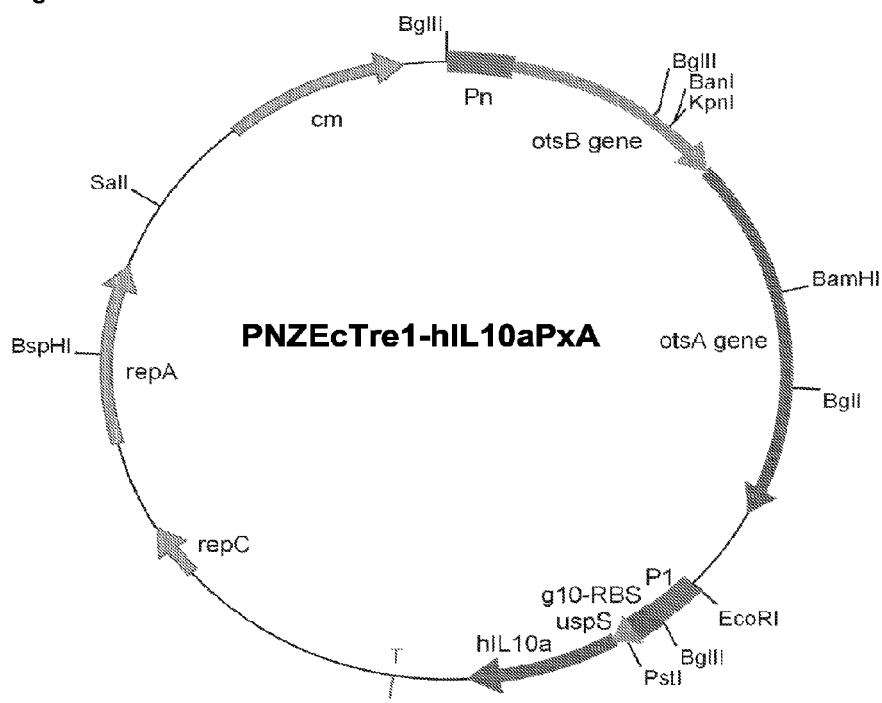
FIG. 11: Plasmid map of pNZEcTre1-hIL10aPxA whereby the otsB/otsA operon is operably linked to the nisin promoter and the hIL-10 secretion cassette is operably linked to the lactococcal P1 promotor.

The plasmid pNZEcTre1-hIL10aPxA is obtained by PCR amplification with Vent® DNA polymerase (NEB) of the hIL-10 expression cassette from the plasmid pT1hIL10aPxA and the following primer sequences: 5'-GC ACTAGTGAATTCGATTAAGTCATCTTACC-3' and 5'-CG ACTAGTTAGTTTCGTATCTTCATTGTCATGTAG-3', in which ACTAGT is a SpeI restriction site. The amplified 796 bp DNA fragment is digested with SpeI, ligated into the XbaI opened pNZEcTre1 plasmid and transformed by electroporation into *L. lactis* strain NZ9000. Transformants are obtained as described by Wells et al (1993). The direction of the cloned hIL-10 expression cassette is sequence-verified (FIG. 11).

Figure 9:
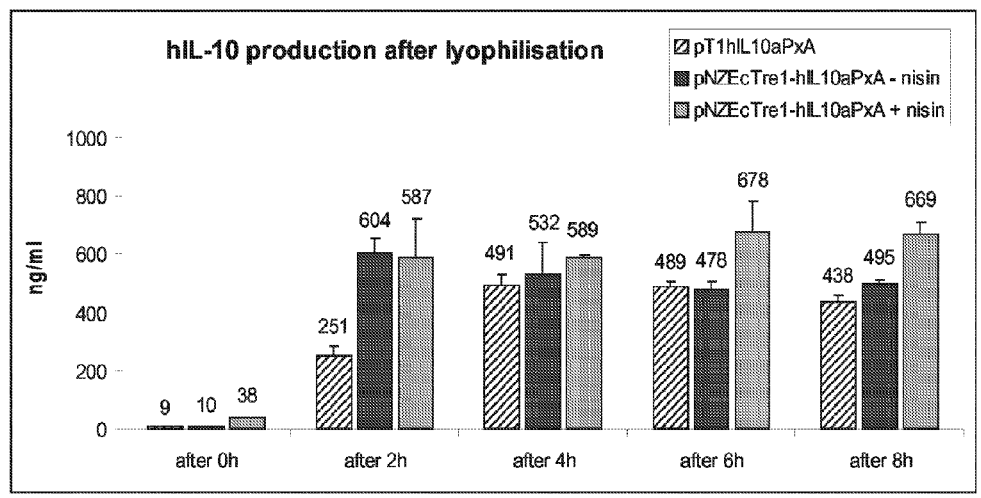
FIG. 9: production of human IL-10 after 8 hrs at 37° C., after freeze drying of the culture and rehydratation, calculated per ml culture, by L. lactis NZ9000 [pNZEcTre1-hIL10aPxA] induced (+nisin) and non-induced (−nisin), in comparison with the non-trehalose accumulating control MG1363 [pT1hIL10aPxA].
Figure 10:
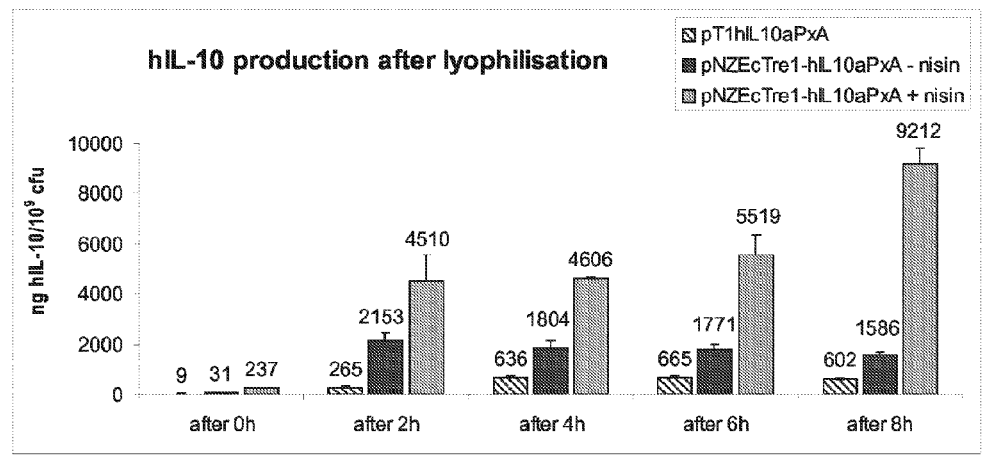
FIG. 10: production of human IL-10 after 8 hrs at 37° C., after freeze drying of the culture and rehydratation, calculated per cfu, by L. lactis NZ9000 [pNZEcTre1-hIL10aPxA] induced (+nisin) and non-induced (−nisin), in comparison with the non-trehalose accumulating control MG1363 [pT1hIL10aPxA].

A saturated overnight culture of *L. lactis* NZ9000 [pNZEcTre1-hIL10aPxA] was induced with nisin (0.4 µg/ml), for 3 hours at 30° C., 200 rpm in an orbital shaker. The same culture without nisin was used as control, as well as a non-induced culture of *L. lactis* MG1363 [pT1hIL10aPxA]. The cultures were freeze dried as described in example 4. After freeze drying, the powder was redissolved in the original volume of 50 mM $CO_3^{2-}$, comprising 0.5% glucose. This solution was incubated at 37° C. Samples were taken after 0, 2, 4 and 6 hours, and the amount of hIL-10 was determined by an ELISA test (Maxisorp F96 plates (Nunc) were coated overnight with rat anti-human IL-10 antibody (BD). The plates were blocked with 0.1% casein solution for 2 hours. Serial dilutions of recombinant hIL-10 standard (BD) and supernatants were loaded on the plates. The bound hIL-10 was detected with biotinylated rat anti-human IL-10 (BD) and horseradish peroxidase coupled streptavidin (BD). The plates were developed with TMB substrate (BD). The reaction was stopped after 30 minutes with 1 M $H_2SO_4$. The absorbance was measured at 450 nm with 595 nm as reference wavelength.) as well as the cfu by plating. The results of the hIL-10 production in function of the culture volume and the number of cfu, after 8 hours of incubation are shown in FIGS. 9 and 10. The production of the trehalose accumulating strain is always higher, independent of the way of calculating the yield, indicating that not only the survival is better, but also the production capacity per cfu.

Tables

TABLE 1

Percentage survival of NZ9000[pNZEcTre1] following freeze-drying

| Storage condition | Storage period | Induced | Non-induced |
|---|---|---|---|
| directly after freeze-drying | | 96% | 47% |
| 8 C. - 10% RH | 1 week | 100% | 49% |
| | 4 weeks | 109% | 37% |
| 8 C. - 60% RH | 1 week | 103% | 15% |
| | 4 weeks | 86% | 6% |
| 20 C. - 10% RH | 1 week | 67% | 19% |
| | 4 weeks | 46% | 8% |

TABLE 2

Effect of trehalose accumulation in nisin induced cultures on survival in different concentrations of oxgall, expressed as colony forming units

| cfu/ml | after 0 h −nisin | after 0 h +nisin | after 0.5 h −nisin | after 0.5 h +nisin | after 2 h −nisin | after 2 h +nisin | after 4 h −nisin | after 4 h +nisin |
|---|---|---|---|---|---|---|---|---|
| before A.C. | $2.68 \times 10^9$ | $1.26 \times 10^9$ | $2.68 \times 10^9$ | $1.26 \times 10^9$ | $2.68 \times 10^9$ | $1.26 \times 10^9$ | $2.68 \times 10^9$ | $1.26 \times 10^9$ |
| after A.C. | $3.16 \times 10^9$ | $1.57 \times 10^9$ | $3.16 \times 10^9$ | $1.57 \times 10^9$ | $3.16 \times 10^9$ | $1.57 \times 10^9$ | $3.16 \times 10^9$ | $1.57 \times 10^9$ |
| 0% oxgall | $3.16 \times 10^9$ | $1.57 \times 10^9$ | $3.44 \times 10^9$ | $1.56 \times 10^9$ | $3.29 \times 10^9$ | $1.48 \times 10^9$ | $2.84 \times 10^9$ | $1.36 \times 10^9$ |
| 0.13% oxgall | $3.38 \times 10^9$ | $1.61 \times 10^9$ | $1.12 \times 10^9$ | $1.07 \times 10^9$ | $2.87 \times 10^6$ | $4.10 \times 10^7$ | $6.00 \times 10^4$ | $1.48 \times 10^7$ |
| 0.33% oxgall | $3.43 \times 10^9$ | $1.30 \times 10^9$ | $1.12 \times 10^7$ | $1.44 \times 10^7$ | $3.00 \times 10^4$ | $7.00 \times 10^4$ | $<1.00 \times 10^3$ | $<1.00 \times 10^3$ |
| 0.67% oxgall | $3.28 \times 10^9$ | $1.41 \times 10^9$ | $3.51 \times 10^7$ | $5.38 \times 10^7$ | $5.06 \times 10^6$ | $2.05 \times 10^5$ | $<1.00 \times 10^3$ | $<1.00 \times 10^3$ |

TABLE 3

Effect of trehalose accumulation in nisin induced cultures on survival in different concentrations of oxgall, expressed as percentage of the initial concentration

| % | after 0 h −nisin | after 0 h +nisin | after 0.5 h −nisin | after 0.5 h +nisin | after 2 h −nisin | after 2 h +nisin | after 4 h −nisin | after 4 h +nisin |
|---|---|---|---|---|---|---|---|---|
| before A.C. | 100% | 100% | 100% | 100% | 100% | 100% | 100% | 100% |
| after A.C. | 118% | 124% | 118% | 124% | 118% | 124% | 118% | 124% |
| 0% oxgall | 118% | 124% | 128% | 123% | 123% | 118% | 106% | 108% |
| 0.13% oxgall | 126% | 128% | 42% | 85% | 0% | 3% | 0% | 1% |
| 0.33% oxgall | 128% | 103% | 0% | 1% | 0% | 0% | 0% | 0% |
| 0.67% oxgall | 122% | 112% | 1% | 4% | 0% | 0% | 0% | 0% |

TABLE 4

Effect of trehalose accumulation in nisin induced cultures on survival of freeze dried cultures in different concentrations of oxgall, expressed as colony forming units

| cfu/ml | after 0 h −nisin | after 0 h +nisin | after 0.5 h −nisin | after 0.5 h +nisin | after 2 h −nisin | after 2 h +nisin | after 4 h −nisin | after 4 h +nisin |
|---|---|---|---|---|---|---|---|---|
| before lyo | $3.33 \times 10^9$ | $1.33 \times 10^9$ | $3.33 \times 10^9$ | $1.33 \times 10^9$ | $3.33 \times 10^9$ | $1.33 \times 10^9$ | $3.33 \times 10^9$ | $1.33 \times 10^9$ |
| after lyo | $2.02 \times 10^9$ | $1.28 \times 10^9$ | $2.02 \times 10^9$ | $1.28 \times 10^9$ | $2.02 \times 10^9$ | $1.28 \times 10^9$ | $2.02 \times 10^9$ | $1.28 \times 10^9$ |
| 0% oxgall | $2.02 \times 10^9$ | $1.28 \times 10^9$ | $2.16 \times 10^9$ | $1.23 \times 10^9$ | $1.72 \times 10^9$ | $1.20 \times 10^9$ | $1.73 \times 10^9$ | $1.10 \times 10^9$ |
| 0.13% oxgall | $1.71 \times 10^9$ | $1.13 \times 10^9$ | $2.04 \times 10^9$ | $1.09 \times 10^9$ | $1.59 \times 10^9$ | $1.21 \times 10^9$ | $1.65 \times 10^9$ | $1.07 \times 10^9$ |
| 0.33% oxgall | $1.93 \times 10^9$ | $1.11 \times 10^9$ | $1.54 \times 10^9$ | $1.08 \times 10^9$ | $1.31 \times 10^9$ | $1.06 \times 10^9$ | $9.15 \times 10^8$ | $9.05 \times 10^8$ |
| 0.67% oxgall | $1.29 \times 10^9$ | $1.07 \times 10^9$ | $1.14 \times 10^9$ | $1.11 \times 10^9$ | $1.04 \times 10^9$ | $7.53 \times 10^8$ | $8.35 \times 10^8$ | $8.41 \times 10^8$ |

TABLE 5

Effect of trehalose accumulation in nisin induced cultures on survival of freeze dried cultures in different concentrations of oxgall, expressed as percentage of the initial concentration

| % | after 0 h −nisin | after 0 h +nisin | after 0.5 h −nisin | after 0.5 h +nisin | after 2 h −nisin | after 2 h +nisin | after 4 h −nisin | after 4 h +nisin |
|---|---|---|---|---|---|---|---|---|
| before lyo | 100% | 100% | 100% | 100% | 100% | 100% | 100% | 100% |
| After Lyo | 61% | 96% | 61% | 96% | 61% | 96% | 61% | 96% |
| 0% oxgall | 61% | 96% | 65% | 92% | 52% | 90% | 52% | 83% |

TABLE 5-continued

Effect of trehalose accumulation in nisin induced cultures on survival of freeze dried cultures in different concentrations of oxgall, expressed as percentage of the initial concentration

| % | after 0 h −nisin | after 0 h +nisin | after 0.5 h −nisin | after 0.5 h +nisin | after 2 h −nisin | after 2 h +nisin | after 4 h −nisin | after 4 h +nisin |
|---|---|---|---|---|---|---|---|---|
| 0.13% oxgall | 51% | 85% | 61% | 82% | 48% | 91% | 50% | 80% |
| 0.33% oxgall | 58% | 83% | 46% | 81% | 39% | 79% | 27% | 68% |
| 0.67% oxgall | 39% | 81% | 34% | 84% | 31% | 57% | 25% | 63% |

TABLE 6

Effect of trehalose accumulation in nisin induced cultures on survival of freeze dried cultures in different concentrations of gastric juice, expressed as colony forming units

| cfu/ml | after 0 h −nisin | after 0 h +nisin | after 0.5 h −nisin | after 0.5 h +nisin | after 1 h −nisin | after 1 h +nisin | after 2 h −nisin | after 2 h +nisin |
|---|---|---|---|---|---|---|---|---|
| before lyo | $2.80 \times 10^9$ | $1.20 \times 10^9$ | $2.80 \times 10^9$ | $1.20 \times 10^9$ | $2.80 \times 10^9$ | $1.20 \times 10^9$ | $2.80 \times 10^9$ | $1.20 \times 10^9$ |
| after lyo | $2.05 \times 10^9$ | $1.17 \times 10^9$ | $2.05 \times 10^9$ | $1.17 \times 10^9$ | $2.05 \times 10^9$ | $1.17 \times 10^9$ | $2.05 \times 10^9$ | $1.17 \times 10^9$ |
| 0% gastric juice | $2.05 \times 10^9$ | $1.17 \times 10^9$ | $1.82 \times 10^9$ | $1.25 \times 10^9$ | $1.75 \times 10^9$ | $1.38 \times 10^9$ | $1.86 \times 10^9$ | $1.20 \times 10^9$ |
| 25% gastric juice | $2.06 \times 10^9$ | $8.54 \times 10^8$ | $1.55 \times 10^8$ | $7.14 \times 10^8$ | $1.03 \times 10^8$ | $6.77 \times 10^7$ | $6.07 \times 10^7$ | $1.58 \times 10^7$ |
| 50% gastric juice | $1.63 \times 10^9$ | $8.33 \times 10^8$ | $1.06 \times 10^8$ | $5.27 \times 10^8$ | $5.81 \times 10^7$ | $3.61 \times 10^7$ | $3.13 \times 10^7$ | $1.29 \times 10^7$ |
| 75% gastric juice | $2.10 \times 10^9$ | $9.54 \times 10^8$ | $1.26 \times 10^7$ | $2.41 \times 10^7$ | $9.00 \times 10^6$ | $1.37 \times 10^7$ | $4.81 \times 10^6$ | $9.18 \times 10^6$ |

TABLE 7

Effect of trehalose accumulation in nisin induced cultures on survival of freeze dried cultures in different concentrations of gastric juice, expressed as percentage of the initial concentration.

| % | after 0 h −nisin | after 0 h +nisin | after 0.5 h −nisin | after 0.5 h +nisin | after 1 h −nisin | after 1 h +nisin | after 2 h −nisin | after 2 h +nisin |
|---|---|---|---|---|---|---|---|---|
| Before lyo | 100% | 100% | 100% | 100% | 100% | 100% | 100% | 100% |
| After lyo | 73% | 98% | 73% | 98% | 73% | 98% | 73% | 98% |
| 0% gastric juice | 73% | 98% | 65% | 104% | 62% | 115% | 67% | 101% |
| 25% gastric juice | 74% | 71% | 6% | 60% | 4% | 6% | 2% | 1% |
| 50% gastric juice | 58% | 70% | 4% | 44% | 2% | 3% | 1% | 1% |
| 75% gastric juice | 75% | 80% | 0% | 2% | 0% | 1% | 0% | 1% |

REFERENCES

Andersson, U., Levander, F. and Radstrom, P. (2001) Trehalose-6-phosphate phosphorylase is part of a novel metabolic pathway for trehalose utilization in *Lactococcus lactis*. J. Biol. Chem., 276, 42707-42713.

Conrad, P. B., Miller, D. P., Cielenski, P. R. and de Pablo, J. J. (2000) Stabilization and preservation of *Lactobacillus acidophilus* in saccharide matrices. Cryobiology 41, 17-24.

Gaudu, P., Vido, K., Cesselin, B., Kulakauskas, S., Tremblay, J., Rezaiki, L., Lambert, G., Sourice, S., Duwat, P and Gruss, A. (2002) Respiration capacity and consequences in *Lactococcus lactis*. Antonie van Leeuwenhoek, 82, 263-269.

Jensen, J. B., Peters, N. K. and Bhuvaneswari, T. V. (2002) Redundancy in periplasmic binding protein-dependent transport systems for trehalose, sucrose and maltose in *Sinorhizobium meliloti*. J. Bacteriol., 184, 2978-2986.

Kaasen, I., McDougall, J. and Strom, A. R. (1994) Analysis of the otsBA operon for osmoregulatory trehalose synthesis in *Escherichia coli* and homology of the OtsA and OtsB proteins to the yeast trehalose-6-phosphate synthase/phosphatase complex. Gene 145, 9-15.

Kuipers, O., De Ruyter, P., Kleerebezem, M. and De Vos, W. (1998) Quorum sensing controlled gene expression in lactic acid bacteria. J. Biotechnol. 64, 15-21.

Li, Y., Hugenholtz, J., Abee, T and Molenaar, D. (2003) Glutathione protects *Lactococcus lactis* against oxidative stress. Appl. Environ. Microbiol., 69, 5739-5745.

Padilla, L., Krämer, R., Stephanopoulos, G and Agosin, E. (2004) Overproduction of trehalose: heterologous expression of *Escherichia coli* trehalose-6-phosphate synthase and trehalose-6-phosphate phosphatase in *Corynebacterium glutamicum*. Appl. Environ. Microbiol., 70, 370-376.

Ruyter, P., Kuipers, O. and De Vos, W. (1996) Controlled gene expression systems for *Lactococcus lactis* with the food-grade inducer nisin. Appl. Environ. Microbiol. 62, 3662-3667.

Schotte, L., Steidler, L., Vandekerckhove, J. and Remaut, E. (2000) Secretion of biologically active murine interleukin-10 bp *Lactococcus lactis*. Enzyme Microb. Technol. 27, 761-765.

Trinder, P. (1969) Determination of blood glucose using 4-aminophenazone as oxygen receptor. J. Clin. Pathol. 22, 246.

Wells, J. M., Wilson, P. W. and Le Page, R. W. (1993) Improved cloning vectors and transformation procedure for *Lactococcus lactis*. J. Appl. Bacteriol. 74, 629-636.

Woodcock, D. M., Crowther, P. J., Doherty, J., Jefferson, S., DeCruz, E., Noyer-Weidner, M., Smith, S. S., Michael, M. Z. and Graham, M. W. (1989) Nucl. Acids Res. 17, 3469-3478.

What is claimed is:

1. An isolated *Lactococcus lactis* strain comprising an internal trehalose concentration of at least 10 mg per gram wet weight of the *L. lactis* cells, wherein the strain expresses a heterologous trehalose-6-phosphate phosphatase gene, and wherein trehalose-6-phosphate phosphorylase activity is inactivated in the *L. lactis* cells.

2. The isolated *Lactococcus lactis* strain according to claim 1, further comprising a heterologous trehalose-6-phosphate synthase gene.

3. The isolated *Lactococcus lactis* strain according to claim 1, wherein said heterologous trehalose-6-phosphate phosphatase gene is situated on a self-replicating plasmid.

4. The isolated *Lactococcus lactis* strain according to claim 1, wherein said heterologous trehalose-6-phosphate phosphatase gene is integrated into the bacterial genome.

5. The isolated *Lactococcus lactis* strain according to claim 1, wherein said heterologous trehalose-6-phosphate phosphatase gene is operably linked to an inducible promoter.

6. The isolated *Lactococcus lactis* strain according to claim 1, wherein said heterologous trehalose-6-phosphate phosphatase gene is operably linked to a constitutive promoter.

7. The isolated *Lactococcus lactis* strain according to claim 1, wherein said heterologous trehalose-6-phosphate phosphatase gene is operably linked to an inducible *Lactococcus lactis* nisin promoter.

8. The isolated *Lactococcus lactis* strain according to claim 1, wherein said trehalose-6-phosphate phosphatase gene is under the control of a *Lactococcus lactis* P1 promoter.

9. The isolated *Lactococcus lactis* strain according to claim 1, wherein said heterologous trehalose-6-phosphate phosphatase gene is the *Escherichia coli* otsB gene.

10. The isolated *Lactococcus lactis* strain according to claim 2, wherein said heterologous trehalose-6-phosphate synthase gene is the *Escherichia coli* otsA gene.

11. The isolated *Lactococcus lactis* strain according to claim 1, comprising an internal trehalose concentration of 10-50 mg per gram wet weight of the *L. lactis* cells.

12. The isolated *Lactococcus lactis* strain according to claim 1, wherein said *Lactococcus lactis* strain has improved storage characteristics compared to a *Lactococcus lactis* strain comprising an internal trehalose concentration of less than 10 mg per gram wet weight of the *L. lactis* cells.

13. The isolated *Lactococcus lactis* strain according to claim 1, wherein said *Lactococcus lactis* strain has improved tolerance to freeze drying compared to a *Lactococcus lactis* strain comprising an internal trehalose concentration of less than 10 mg per gram wet weight of the *L. lactis* cells.

14. The isolated *Lactococcus lactis* strain according to claim 1, wherein said *Lactococcus lactis* strain has improved tolerance to acidic conditions compared to a *Lactococcus lactis* strain comprising an internal trehalose concentration of less than 10 mg per gram wet weight of the *L. lactis* cells.

15. The isolated *Lactococcus lactis* strain according to claim 14, wherein said *Lactococcus lactis* strain has improved tolerance to human gastric juice.

16. The isolated *Lactococcus lactis* strain according to claim 1, wherein said *Lactococcus lactis* strain has improved tolerance to bile salts compared to a *Lactococcus lactis* strain comprising an internal trehalose concentration of less than 10 mg per gram wet weight of the *L. lactis* cells.

17. The isolated *Lactococcus lactis* strain according to claim 1, wherein said *Lactococcus lactis* strain has an improved production capacity for producing a heterologous biologically active polypeptide per colony forming unit (cfu) compared to a *Lactococcus lactis* strain comprising an internal trehalose concentration of less than 10 mg per gram wet weight of the *L. lactis* cells.

18. The isolated *Lactococcus lactis* strain according to claim 1, wherein said internal trehalose concentration is measured using a method comprising converting said trehalose to glucose, and measuring said glucose.

* * * * *

```
                        SEQUENCE LISTING

<160> NUMBER OF SEQ ID NOS: 11

<210> SEQ ID NO 1
<211> LENGTH: 32
<212> TYPE: DNA
<213> ORGANISM: Artificial Sequence
<220> FEATURE:
<223> OTHER INFORMATION: forward primer
<220> FEATURE:
<221> NAME/KEY: misc_feature
<222> LOCATION: (9)..(11)
<223> OTHER INFORMATION: initiator codon of the otsB cistron
<220> FEATURE:
<221> NAME/KEY: misc_feature
<222> LOCATION: (3)..(8)
<223> OTHER INFORMATION: NcoI restriction site

<400> SEQUENCE: 1
gcccatgggt gacagaaccg ttaaccgaaa cc                            32

<210> SEQ ID NO 2
<211> LENGTH: 32
<212> TYPE: DNA
<213> ORGANISM: Artificial Sequence
<220> FEATURE:
<223> OTHER INFORMATION: reverse primer
<220> FEATURE:
<221> NAME/KEY: misc_feature
<222> LOCATION: (3)..(8)
<223> OTHER INFORMATION: XbaI restriction site
<220> FEATURE:
<221> NAME/KEY: misc_feature
<222> LOCATION: (9)..(11)
<223> OTHER INFORMATION: the complement of the TAG stop codon of the
      otsA cistron

<400> SEQUENCE: 2
gctctagact acgcaagctt tggaaaggta gc                            32

<210> SEQ ID NO 3
<211> LENGTH: 23
<212> TYPE: DNA
<213> ORGANISM: Artificial Sequence
<220> FEATURE:
<223> OTHER INFORMATION: recombinant plasmid
<220> FEATURE:
<221> NAME/KEY: misc_feature
<222> LOCATION: (11)..(13)
<223> OTHER INFORMATION: the second amino acid residue of OtsB

<400> SEQUENCE: 3
ggcactcacc atgggtgaca gaa                                      23

<210> SEQ ID NO 4
<211> LENGTH: 28
<212> TYPE: DNA
<213> ORGANISM: Artificial Sequence
<220> FEATURE:
<223> OTHER INFORMATION: forward primer

<400> SEQUENCE: 4
```
ggcactcacc atgacagaac cgttaacc                              28

<210> SEQ ID NO 5
<211> LENGTH: 32
<212> TYPE: DNA
<213> ORGANISM: Artificial Sequence
<220> FEATURE:
<223> OTHER INFORMATION: reverse primer
<220> FEATURE:
<221> NAME/KEY: misc_feature
<222> LOCATION: (3)..(8)
<223> OTHER INFORMATION: a XbaI restriction site
<220> FEATURE:
<221> NAME/KEY: misc_feature
<222> LOCATION: (9)..(11)
<223> OTHER INFORMATION: the complement of the TAG stop codon of the
      otsA cistron

<400> SEQUENCE: 5
gctctagact acgcaagctt tggaaaggta gc                         32

<210> SEQ ID NO 6
<211> LENGTH: 33
<212> TYPE: DNA
<213> ORGANISM: Artificial Sequence
<220> FEATURE:
<223> OTHER INFORMATION: forward primer
<220> FEATURE:
<221> NAME/KEY: misc_feature
<222> LOCATION: (3)..(8)
<223> OTHER INFORMATION: coincides with the SalI restriction site in
      pNZEcTre0

<400> SEQUENCE: 6
gcgtcgacgg caatagttac ccttattatc aag                        33

<210> SEQ ID NO 7
<211> LENGTH: 28
<212> TYPE: DNA
<213> ORGANISM: Artificial Sequence
<220> FEATURE:
<223> OTHER INFORMATION: reverse primer
<220> FEATURE:
<221> NAME/KEY: misc_feature
<222> LOCATION: (16)..(18)
<223> OTHER INFORMATION: CAT is the complement of the initiator codon
      preceding otsB

<400> SEQUENCE: 7
ggttaacggt tctgtcatgg tgagtgcc                              28

<210> SEQ ID NO 8
<211> LENGTH: 33
<212> TYPE: DNA
<213> ORGANISM: Artificial Sequence
<220> FEATURE:
<223> OTHER INFORMATION: primer

<400> SEQUENCE: 8
gcgtcgacgg caatagttac ccttattatc aag                        33

<210> SEQ ID NO 9
<211> LENGTH: 32
<212> TYPE: DNA
<213> ORGANISM: Artificial Sequence
<220> FEATURE:
<223> OTHER INFORMATION: primer

<400> SEQUENCE: 9

```
gctctagact acgcaagctt tggaaaggta gc                                     32

<210> SEQ ID NO 10
<211> LENGTH: 31
<212> TYPE: DNA
<213> ORGANISM: Artificial Sequence
<220> FEATURE:
<223> OTHER INFORMATION: primer for construction of pNZEcTre1-hIL10aPxA

<400> SEQUENCE: 10
gcactagtga attcgattaa gtcatcttac c                                      31

<210> SEQ ID NO 11
<211> LENGTH: 35
<212> TYPE: DNA
<213> ORGANISM: Artificial Sequence
<220> FEATURE:
<223> OTHER INFORMATION: primer for construction of pNZEcTre1-hIL10aPxA

<400> SEQUENCE: 11
cgactagtta gtttcgtatc ttcattgtca tgtag                                  35
```